United States Patent
Styrc et al.

(12)

(10) Patent No.: US 8,252,037 B2
(45) Date of Patent: Aug. 28, 2012

(54) DEVICE FOR TREATING A DUCT THROUGH WHICH BLOOD FLOWS AND ASSOCIATED PREPARATION METHOD

(75) Inventors: Mikolaj Vitold Styrc, Echternach (LU); Eric Perouse, Paris (FR)

(73) Assignee: Laboratoires Perouse, Ivry le Temple (FR)

( * ) Notice: Subject to any disclaimer, the term of this patent is extended or adjusted under 35 U.S.C. 154(b) by 401 days.

(21) Appl. No.: 12/223,170

(22) PCT Filed: Jan. 23, 2007

(86) PCT No.: PCT/FR2007/000129
§ 371 (c)(1),
(2), (4) Date: Jun. 3, 2010

(87) PCT Pub. No.: WO2007/085724
PCT Pub. Date: Aug. 2, 2007

(65) Prior Publication Data
US 2010/0268322 A1  Oct. 21, 2010

(30) Foreign Application Priority Data
Jan. 24, 2006 (FR) .................................... 06 00654

(51) Int. Cl.
*A61F 2/06* (2006.01)
(52) U.S. Cl. ..................... 623/1.11; 623/1.23
(58) Field of Classification Search ............... 623/1.11, 623/1.12, 1.1, 1.23, 1.15, 1.16; 606/108, 606/192, 194, 195
See application file for complete search history.

(56) References Cited

U.S. PATENT DOCUMENTS

| 5,464,449 A | 11/1995 | Ryan et al. |
| 5,693,083 A | 12/1997 | Baker et al. |
| 5,749,920 A | 5/1998 | Quiachon et al. |
| 2003/0004560 A1 | 1/2003 | Chobotov et al. |

FOREIGN PATENT DOCUMENTS

| EP | 0 707 462 | 1/1995 |
| WO | 02/083038 | 10/2002 |

OTHER PUBLICATIONS

International Search Report mailed Jul. 17, 2007, in the International (PCT) Application of which the present application is the U.S. National Stage.

*Primary Examiner* — Kathleen Sonnett
*Assistant Examiner* — Jocelin Tanner
(74) *Attorney, Agent, or Firm* — Wenderoth, Lind & Ponack, L.L.P.

(57) ABSTRACT

This device comprises a tubular endoprosthesis (11) of axis (X-X') and a stent (13) of axis (Y-Y') defining a distal retention opening (23A) and a proximal retention opening (23B). The device comprises a distal wire-like tie (33A) and a proximal wire-like tie (33B). Each tie (33A, 33B) forms a retaining loop (43) running around the endoprosthesis (11). Each retaining loop (43) can stretch between a configuration in which the endoprosthesis (11) is kept in a contracted state against the stent (13) and a configuration in which the endoprosthesis (11) is released. When each retaining loop (43) is in its releasing configuration, the axis (X-X') of the endoprosthesis (11) is inclined with respect to the axis (Y-Y') of the stent (13) when no external stresses are applied. The axis (X-X') of the endoprosthesis (11) intersects the axis (Y-Y') of the stent in the internal line (18) defined by the endoprosthesis (11).

20 Claims, 2 Drawing Sheets

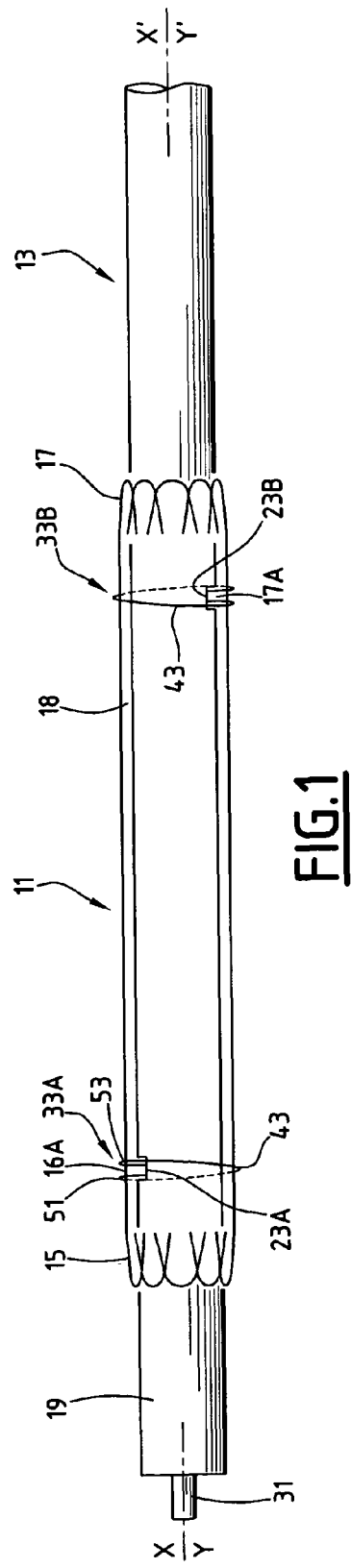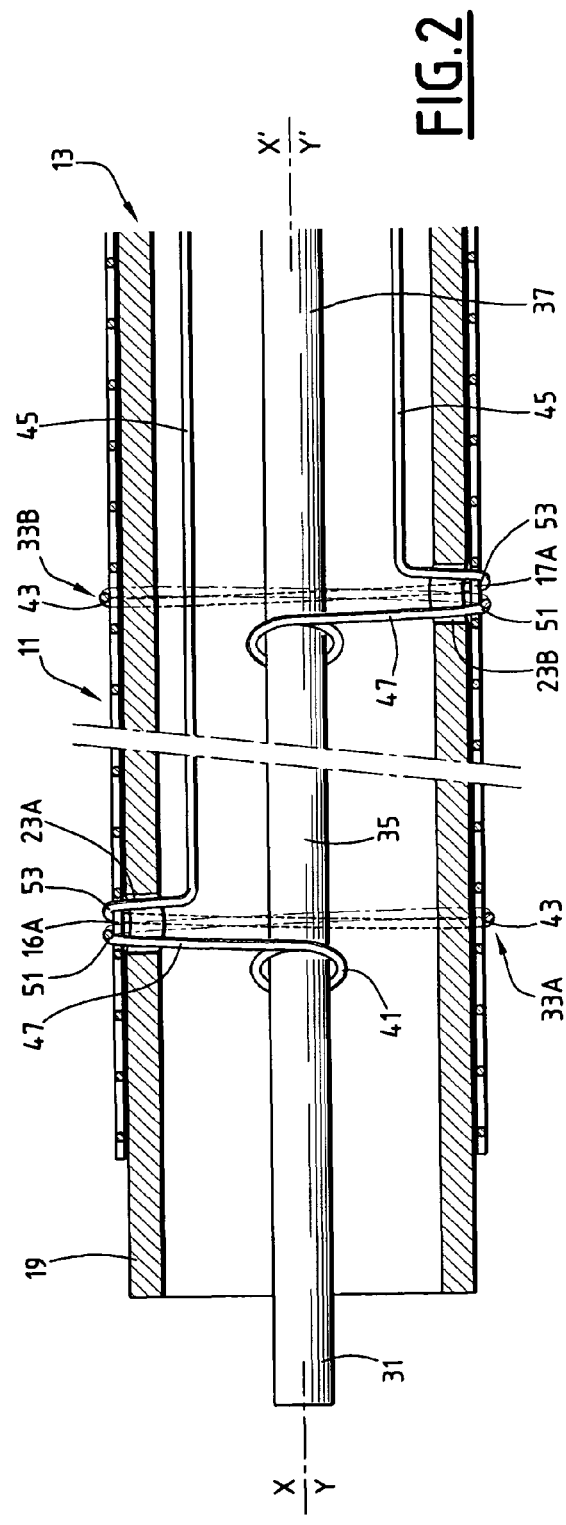

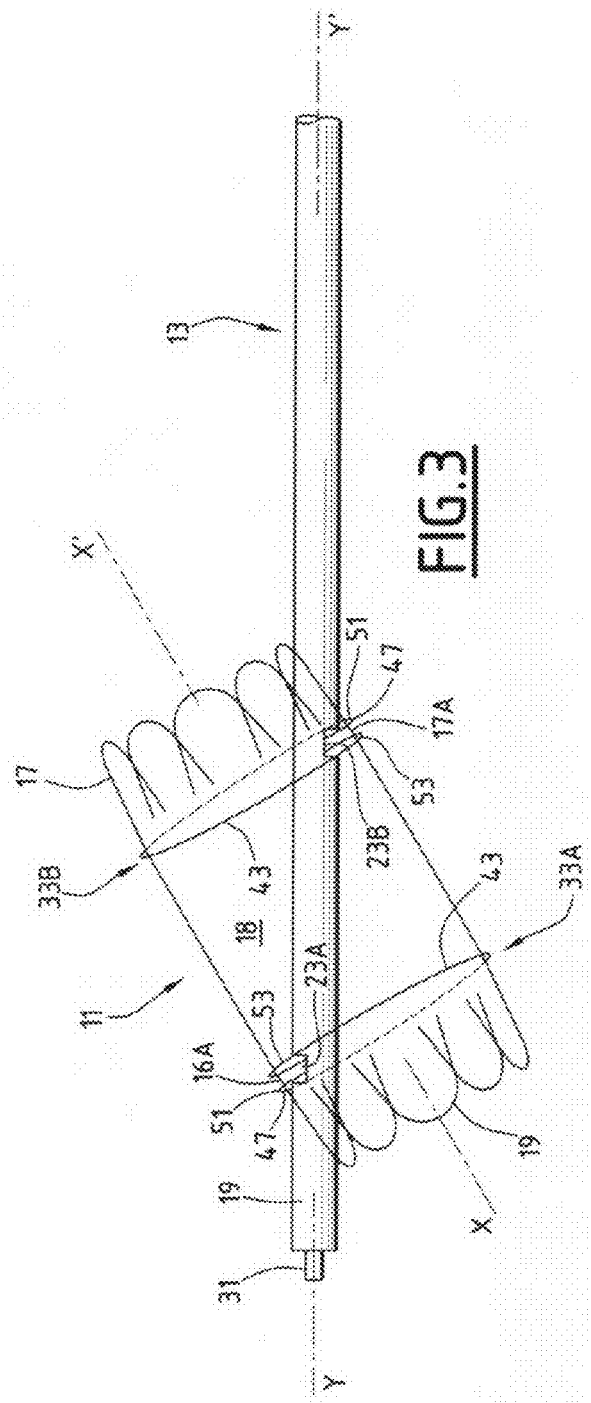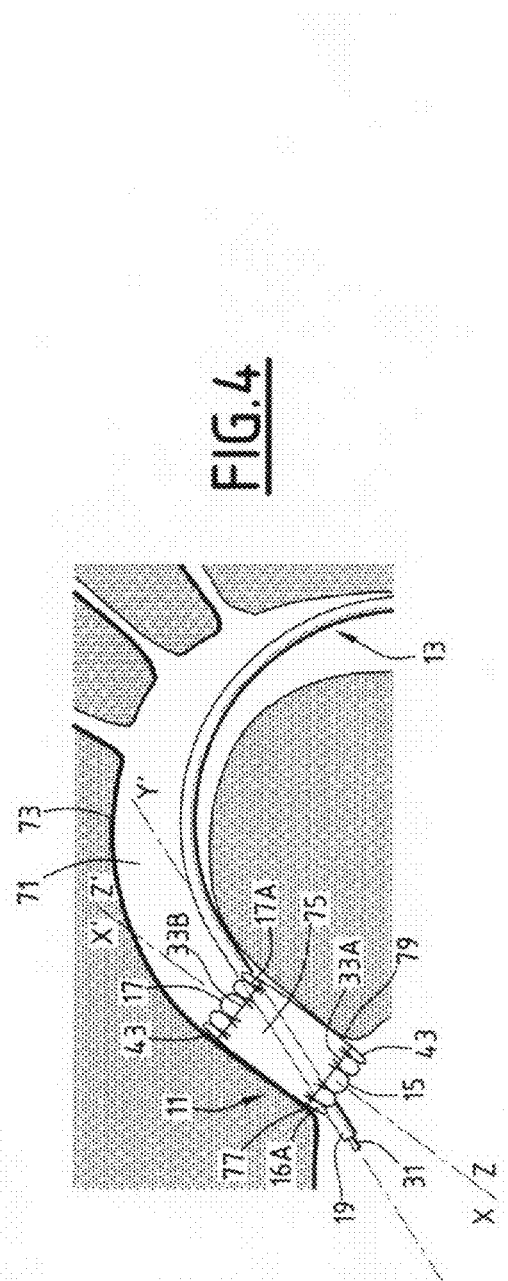

DEVICE FOR TREATING A DUCT THROUGH WHICH BLOOD FLOWS AND ASSOCIATED PREPARATION METHOD

The present invention relates to a device for treating a duct through which blood flows, of the type comprising:
- at least one tubular endoprosthesis of axis X-X', capable of extending radially between a contracted state and a dilated state, the endoprosthesis defining an internal duct through which blood flows;
- a prop of axis Y-Y' defining at least one proximal retention opening and at least one distal retention opening;
- a distal wire-like tie and a proximal wire-like tie engaged respectively in the distal retention opening and in the proximal retention opening, each tie forming a retaining loop encircling the endoprosthesis, each retaining loop being extendible between a configuration in which the endoprosthesis is kept in its contracted state against the stent, and a configuration in which the endoprosthesis is released and in which the endoprosthesis is substantially in its dilated state.

Such a device is used to install tubular endoprosthesis into a blood vessel, these endoprosthesis being commonly denoted by the English word "stent", or tubular endovalves, comprising a tubular endoprosthesis and a valve fixed to the endoprosthesis.

A device of the aforementioned type is described in EP A 0 707 462. An endoprosthesis is coaxially mounted on two hollow props which are able to slide inside one another. This endoprosthesis is kept in its retracted state by means of two wire-like ties which encircle the ends thereof. The wire-like ties are engaged in the distal and proximal retention openings respectively which are arranged in each of the respective props.

To install the endoprosthesis, the props are displaced by sliding relative to one another, in such a way that the distance between the retention openings decreases.

The decrease in this distance causes the wire-like ties to loosen and consequently the two ends of the endoprosthesis simultaneously extend. The endoprosthesis thus extends from its retracted state to its dilated state, which is substantially coaxial with respect to the stent.

Such a device is therefore suitable when the blood vessel is substantially linear in the region where the endoprosthesis extends.

However, when the endoprosthesis is to be extended in a bent blood vessel, for example in an artery connected to the heart, the relative rigidity of the prop does not allow the endoprosthesis to be kept substantially parallel to the axis of the blood vessel at the point of extension of the endoprosthesis.

Since extension of the endoprosthesis is coaxial with respect to the axis of the stent, the positioning thereof in the blood vessel is difficult and laborious.

An object of the invention is therefore to provide a device for treating a blood vessel which may be positioned more precisely in a bent blood vessel.

The invention accordingly relates to a treatment device of the aforementioned type, characterised in that when each retaining loop is in its releasing configuration, the axis of the endoprosthesis is inclined with respect to the axis of the prop when no external stresses are applied, the axis of the endoprosthesis intersecting the axis of the prop in the internal line.

The device according to the invention may comprise one or more of the following characteristics, taken in isolation or according to all technically possible combinations:
- the endoprosthesis defines a proximal guidance passage and a distal guidance passage, located respectively on two generatrixes of the endoprosthesis which are angularly offset about the axis of the endoprosthesis, each retaining loop having two ends engaged through one of the guidance passages;
- the proximal guidance passage and the distal guidance passage are substantially located in a axial plane which contains the axis of the endoprosthesis;
- when each retaining loop is in its releasing configuration, the proximal guidance passage and the distal guidance passage are located in the region of the prop, substantially along the axis of the prop;
- the distal retention opening is located opposite the proximal retention opening with respect to the prop, the distal guidance passage being placed in register with the distal retention opening and the proximal guidance passage being located in register with the proximal retention opening;
- a proximal retaining loop extends radially away from the prop in a first direction, between the configuration in which the endoprosthesis is kept in the contracted state and the configuration in which the endoprosthesis is released, a distal retaining loop extending radially away from the prop between the configuration in which the endoprosthesis is kept in the contracted state and the configuration in which the endoprosthesis is released in a second direction away from the first direction;
- the prop has a proximal end, and a distal end in the region of which the retention openings are kept, each wire-like tie having a control portion attached to a first end of the retaining loop and extending to the proximal end of the stent; and
- it comprises a retention rod which is disposed so as to be movable with respect to the prop between a retention position in which an active part of the rod is placed in register with each retention opening and a release position in which the active part of the rod is placed apart from each retention opening, each wire-like tie comprising a keeper loop attached to a second end of the retaining loop and engaged on the rod in its retention position.

The invention further relates to a method for preparing a device as defined above, prior to the implantation thereof into a duct through which blood flows, characterised in that it comprises the following steps:
(a) keeping the endoprosthesis in a dilated state where the or each retaining loop is kept in the configuration thereof in which the endoprosthesis is released, the axis of the endoprosthesis being inclined with respect to the axis of the prop when no external stresses are applied, the axis of the endoprosthesis intersecting the axis of the prop in the internal line; then
(b) tightening each retaining loop to bring it into the configuration thereof in which the endoprosthesis is kept in its contracted state against the prop, in order to implant the endoprosthesis into the duct through which the blood flows.

The invention will be better understood from the following description, given only by way of example and with reference to the accompanying drawings, in which:

FIG. 1 is a schematic side view of a treatment device according to the invention, the endoprosthesis being kept in its retracted state;

FIG. 2 is an enlarged cross-sectional view along an axial median plane of the device in FIG. 1;

FIG. 3 is a view similar to FIG. 1, the endoprosthesis being in its dilated state; and FIG. 4 is a partial schematic cross-sectional view of the device from FIG. 3 during implantation in a bent blood vessel.

The device shown in FIGS. 1 to 4 has a tubular endoprosthesis 11 mounted on a single prop 13 and connected to this prop 13 by releasable retention means.

The endoprosthesis 11 comprises a tubular lattice of axis X-X' made of a superelastic material. This endoprosthesis is therefore auto-extendible. The lattice is partially shown in FIGS. 1 to 4.

This endoprosthesis is made, for example, by weaving a single wire of a superelastic material, as described in the European patent application EP A 0 857 471.

The lattice of the endoprosthesis defines, in the region of a distal end 15 of the endoprosthesis 11, a distal guidance passage 16A for the retention means, and in the region of a proximal end 17 of the endoprosthesis 11, a proximal guidance passage 17A for the retention means.

Each guidance passage 16A, 17A is delimited by a mesh of the lattice of the endoprosthesis. The passages 16A, 17A are located respectively on two generatrixes of the endoprosthesis 11 which are offset angularly about the axis X-X' of the endoprosthesis 11. In this example, the passages 16A, 17A are substantially located in a single plane containing the axis X-X', on each side of the axis X-X'.

In a variant, the passages 16A, 17A are defined by rings which are connected to or formed in the lattice and are disposed in the duct 18.

As is known per se, the endoprosthesis 11 may be spontaneously deformed from a compressed state in which it has a small diameter (FIG. 1) to a dilated state in which it has a larger diameter (FIG. 3), this dilated state being its rest state.

At the ends 15, 17 of the endoprosthesis, the lattice has folded wires which form bends.

The endoprosthesis 11 internally defines a duct 18 of axis X-X' through which blood flows.

In the example shown in FIGS. 1 and 2, the prop 13 comprises a hollow flexible tube. The internal diameter of the tube is suitable for slipping the tube onto a wire-like surgical guide (not shown) installed in the patient, prior to the endoprosthesis 11 being positioned in this patient's blood vessel.

The prop 13 extends longitudinally between a distal end 19 which is intended to be implanted in the blood vessel and a proximal end (not shown) which is intended to be accessible for a surgeon.

Distal and proximal openings 23A and 23B, offset longitudinally, are arranged laterally in the prop 13 in the region of the distal end 19.

In this example, the openings 23A and 23B are arranged in a median longitudinal plane of the prop 13 on each side of an axis Y-Y' of the prop 13. The distance separating the distal retention opening 23A from the proximal retention opening 23B is substantially equal to the length of the endoprosthesis 11 in its retracted state, taken along the axis X-X'. The distal retention opening 23A extends in register with the distal guidance passage 16A, and the proximal retention opening 23B extends in register with the proximal guidance passage 17A.

As described in the Applicant's application FR A 2 863 160, the prop 13 also has hollow outlets (not shown) in the region of its proximal end. These outlets communicate with the inside of the prop 13. A control passage is arranged at a free end of each outlet.

The releasable retention means of the endoprosthesis 11 comprise a retention rod 31 and distal and proximal retention wires 33A and 33B.

The retention rod 31 is disposed inside the prop 13. The length of the rod 31 is greater than or equal to the distance between the distal retention opening 23A and the proximal end of the prop 13. As shown in FIG. 2, the rod comprises an active part 35 and an activating part 37.

The rod 31 is movable in translation along the axis of the prop Y-Y' inside the prop 13, between a retention position in which the active part 35 of the rod is located in register with the two retention openings 23A and 23B, an intermediate position in which the active part 35 is located in register with the proximal retention opening 23B and apart from the distal retention opening 23A and a release position in which the active part is located apart from the two retention openings 23A and 23B.

In the example shown in FIG. 2, the distal retention wire 33A comprises a single thread, which includes an end keeper loop 41, a retaining loop 43 and a control portion 45.

The end keeper loop 41 is formed at a distal end of the thread. It is composed of a closed loop with a small diameter. The active part 35 of the rod 31 is engaged in the keeper loop 41 when the rod 31 is in its retention position.

The keeper loop 41 can also be deformed in such a way that its width, when deformed, is substantially equal to twice the width of the thread.

The keeper loop 41 is connected to the retention loop 43 by a portion 47, engaged in the distal retention opening 23A and in the distal guidance passage 16A.

As shown in FIG. 1, the retaining loop 43 is formed by a portion of the thread, slidingly engaged about the lattice of the endoprosthesis 11, along a circumference of this endoprosthesis 11, about the axis X-X'. In a variant, the retaining loop 43 passes in succession to the inside and the outside of the lattice about the axis X-X'.

The retaining loop 43 extends between a retention end 51 connected to the keeper loop 41 and a retention end 53 connected to the control portion 45. The retention end 53 is engaged in the guidance passage 16A and in the retention opening 23A.

The retaining loop 43 fixes the endoprosthesis 11 to the prop 13 in the region of the distal end 19 of this prop 13.

Furthermore, the active length of the retention loop 43 is variable, in such a way that it controls the extension of the endoprosthesis 11 with respect to the prop 13.

As will be described below, the retaining loop 43 may extend between a configuration in which the endoprosthesis is kept in its contracted state against the prop 13, where the length and diameter of said loop are at their smallest, and a configuration in which the endoprosthesis is released, where the length and diameter of said loop are at their largest.

As shown in FIG. 2, the control portion 45 extends inside the prop 13 between the distal retention opening 23A and a control passage located at the proximal end of the prop 13.

One control end of the control portion 45 is engaged outside the prop 13 through the control passage. A part of this portion therefore protrudes outside the outlet. The length of this protruding part is variable and controls the length of the retaining loop.

Displacement of the control portion 45, with respect to the prop 13, towards the proximal end of the prop, therefore decreases the active length of the retaining loop 43, and consequently the endoprosthesis fastens against the prop 13 in the region of the retaining loop 43.

When the endoprosthesis 11 is in its retracted state against the prop 13, the control portion 45 is held under tension.

On the other hand, displacement of the control portion 45 with respect to the prop 13 towards the distal end 19 of the prop increases the active length of the retaining loop 43 radially away from the axis Y-Y' of the prop 13 and away from the distal guidance passage 16A in a first direction orientated towards the bottom in FIG. 1. This extension of the loop 43 allows the endoprosthesis 11 to extend away from the prop 13, around the retaining loop 43.

When the endoprosthesis 11 is in its dilated state, the control portion 45 is substantially expanded.

As shown in FIG. 2, the structure of the proximal retention wire 33B is similar to that of the distal retention wire 33A.

However, unlike the distal retention wire 33A, the displacement of the control portion 45 of the proximal retention wire 33B with respect to the prop 13, towards the distal end 19 of the prop 13 increases the active length of the retaining loop 43 radially away from the prop 13, and the proximal guidance passage 17A in a second direction opposite the first direction, orientated towards the top in FIG. 1.

As shown in FIG. 3, when the endoprosthesis 11 is in its dilated state, and when the retaining loops 43 are in their expanded configurations in which the endoprosthesis 11 is released, the axis X-X' of the endoprosthesis 11 is inclined with respect to the axis Y-Y' of the prop when no external stresses are applied to the endoprosthesis 11 and/or on the prop 13.

The axis X-X' of the endoprosthesis intersects the axis Y-Y' of the prop in the internal duct 18; in other words, in a projection in a median axial plane passing through axis Y-Y' of the prop, the axis X-X' of the endoprosthesis cuts the axis Y-Y' at a point located inside the duct 18 of flow.

In this configuration, the distal guidance passage 16A and the proximal guidance passage 17A are located in the region of the prop 13, substantially along the axis of the prop Y-Y'. This incline of the endoprosthesis 11 with respect to the prop 13 is spontaneously obtained, for example outside the human body, without the need to apply an external stress to the endoprosthesis 11.

An example of the functioning of the first treatment device according to the invention will now be explained.

Firstly, the device is kept in a packaging (not shown), with the endoprosthesis 11 in an extended state similar to that shown in FIG. 3.

In this configuration, the control rod 31 is in its retention position. The distal and proximal retention wires 23A and 23B are engaged in the rod 31 and in the lattice of the endoprosthesis 11.

This packaging maintains the mechanical properties of the endoprosthesis 11, particularly when the tubular lattice thereof is sunk in a tight and extendible film such as an elastomer.

In this state, the axis X-X' of the endoprosthesis 11 is spontaneously inclined with respect to the axis Y-Y' of the prop 13, as previously described.

Secondly, the surgeon takes the device out of its packaging. He implants a surgical guide (not shown) which extends into a blood vessel 71 from the external point of introduction to the region of the vessel in which the tubular endoprosthesis 11 must be implanted.

As shown in FIG. 4, this vessel 71 has a bend 73 at the point of implantation 75.

Thirdly, in order to implant the endoprosthesis 11 into the blood vessel 71, the surgeon displaces the control portion 45 of each retention wire 23A, 23B towards the proximal end of the prop 13. The active length of the retaining loops 43 decreases in such a way that the endoprosthesis 11 is retracted against the prop 13 and fixed solidly with respect to the prop 13, coaxially with respect to the prop 13.

The endoprosthesis 11 is therefore in the retracted state shown in FIG. 1 in which the lattice is substantially resting against the prop 13. It is thus introduced into its location for implantation by displacing the prop 13 along the surgical guide (not shown).

In some cases, and in order to keep a minimal radial space requirement, a socket (not shown) is placed around the endoprosthesis 11, prior to this insertion, and is withdrawn once the insertion has been effected.

The prop 13 is thus positioned in such a way that the proximal guidance passage 16A is located in the region of a first surface 77 of the vessel to be treated, whereas the distal guidance passage 17A is located in the region of a surface 79 in register with the vessel to be treated. The guidance passages 16A and 17A are placed substantially along the axis Y-Y'.

Taking into account the relative rigidity of the prop 13 when it is implanted in the vessel 71, the prop 13 does not follow the shape of the vessel 71 in the bend 73. At the point of implantation 75, the axis Y-Y' of the prop is inclined with respect to the axis Z-Z' of the vessel 71.

Depending on the shape of the vessel to be treated, the surgeon may choose to first extend one or the other of the ends 15 and 17 of the endoprosthesis 11. By way of example, the extension of the distal end 15 will be described.

Firstly, the surgeon displaces the control portion 45 towards the distal end 19 of the prop 13. The active length of the retaining loop 43 therefore increases.

During this extension of the retaining loop 43, the distal guidance passage 16A is kept substantially in the region of the first surface 77 of the vessel to be treated, and in the region of the prop 13, whereas the retaining loop 43 is extended away from the prop 13 and the distal guidance passage 16A towards the second surface 79 of the vessel to be treated.

The lattice of the endoprosthesis 11 therefore deforms spontaneously from the compressed state shown in FIG. 1 to the extended state shown in FIG. 3.

If the surgeon is not satisfied with the positioning of the distal end 15 of the endoprosthesis 11 when the endoprosthesis is extended, he decreases the active length of the retaining loop 43 by pulling on the control portion 45 in order to compress the endoprosthesis 11 against the prop 13. The endoprosthesis 11 is therefore displaced to a more satisfactory position.

Similarly, the surgeon then carries out the extension of the proximal end 17 of the endoprosthesis 11, by means of the proximal retention wire 33B.

The retaining loop 43 of the proximal retention wire 33B is extended away from the proximal guidance passage 17A towards the opposite surface 77 of the vessel to be treated. When extended, the distal and proximal retaining loops 43 therefore extend across the axis Y-Y' of the stent.

Thus, when the endoprosthesis 11 is in its dilated configuration in the vessel 71, it has an axis X-X' which is substantially parallel to the axis Z-Z' of the vessel 71 at the point of implantation 75.

When the surgeon is satisfied with the positioning of the distal end 15 of the endoprosthesis 11, he displaces the retention rod 31 from its retention position to the intermediate position. During this displacement, the keeper loop 41 of the distal retention wire 33A is released from the rod 31.

The surgeon then pulls on the control portion 45 to bring the distal end of the distal retention wire 23A to the control passage, in succession through the distal guidance passage 16A, around the lattice of the endoprosthesis 11, to the inside of the prop 13, and through the control outlet.

The distal end 15 of the endoprosthesis 11 is therefore irreversibly fixed in the blood vessel 71.

The surgeon therefore checks the positioning of the proximal end 17 of the endoprosthesis 11.

When this end 17 is satisfactorily positioned, he displaces the rod 31 from the intermediate position to the release position and releases the keeper loop 41 from the proximal retention wire 33B.

He withdraws the proximal retention wire 33B as previously described for the distal retention wire 33A. The endoprosthesis 11 is disposed resting on the walls of the blood vessel 71 and the prop 13 is free with respect to the endoprosthesis 11. It is therefore withdrawn outside the blood vessel.

Because of the spontaneous incline of the axis X-X' of the endoprosthesis 11 with respect to the axis Y-Y' of the prop 13 when the retaining loops 43 of the wire-like ties 33A, 33B encircling the endoprosthesis are in a configuration in which the endoprosthesis 11 is released, the positioning of the endoprosthesis 11 in a bent blood vessel 71 is facilitated. Indeed, the axis X-X' of the endoprosthesis 11 in its dilated state is distinct from the axis Y-Y' of the prop 13 and is substantially coincident with the axis Z-Z' of the blood vessel 71 to be treated in the region of the point of implantations 75.

In a variant, the prop 13 may comprise two telescopic portions, movable with respect to one another in translation along the axis Y-Y' of the prop 13, and in rotation about the axis Y-Y' of the prop 13.

The invention claimed is:

1. Device for treating a duct through which blood flows, the device comprising:
    at least one tubular endoprosthesis of longitudinal axis X-X', which can extend radially between a contracted state and a dilated state, the endoprosthesis defining an internal duct through which blood flows;
    a prop of longitudinal axis Y-Y' defining at least one proximal retention opening and at least one distal retention opening;
    a wire-like distal tie and a wire-like proximal tie, engaged respectively in the distal retention opening and in the proximal retention opening, each tie forming a retaining loop encircling the endoprosthesis, each retaining loop being extendible between a configuration in which the endoprosthesis is kept in its contracted state against the prop, and a configuration in which the endoprosthesis is released and in which the endoprosthesis is substantially in its dilated state, wherein, when each retaining loop is in its release configuration, the longitudinal axis X-X' of the endoprosthesis is inclined with respect to the axis Y-Y' of the prop when no external stresses are applied, the lonfitudinal axis X-X' of the endoprosthesis intersecting the axis of the prop in the internal duct.

2. Device according to claim 1, wherein the endoprosthesis defines a proximal guidance passage and a distal guidance passage located respectively on two generatrixes of the endoprosthesis which are offset angularly about the longitudinal axis X-X' of the endoprosthesis, each retaining loop having two ends engaged through one of the guidance passages.

3. Device according to claim 2, wherein a proximal retaining loop extends radially away from the prop in a first direction, between the configuration in which the endoprosthesis is kept in the contracted state and the configuration in which the endoprosthesis is released, a distal retaining loop extending radially away from the prop, between the configuration in which the endoprosthesis is kept in the contracted state and the configuration in which the endoprosthesis is released, in a second direction away from the first direction.

4. Device according to claim 2, wherein the prop has a proximal end and a distal end in the region of which the retention openings are arranged, each wire-like tie comprising a control portion connected to a first end of the retaining loop and extending to the proximal end of the prop.

5. Method of preparation of a device according to claim 2, prior to its implantation in a duct through which blood flows, comprising the following steps:
    (a) keeping the endoprosthesis in a dilated state where the or each retaining loop is kept in its configuration in which the endoprosthesis is released, the longitudinal axis X-X' of the endoprosthesis being inclined with respect to the longitudinal axis Y-Y' of the prop when no external stresses are applied, the longitudinal axis X-X' of the endoprosthesis intersecting the longitudinal axis Y-Y' of the prop in the internal duct; then
    (b) tightening each retaining loop to bring it into the configuration thereof in which the endoprosthesis is kept in its contracted state against the prop, in order to implant the endoprosthesis in the duct through which the blood flows.

6. Method for implanting a device according to claim 2, in a duct through which blood flows, comprising the following steps:
    introducing the endoprosthesis in its contracted state resting against the prop, the endoprosthesis being fixed substantially coaxially with the prop;
    extending the retaining loops of the wire-like distal tie and of the wire-like proximal tie to pass the endoprosthesis in its dilated state, the longitudinal axis X-X' of the endoprosthesis being inclined with the longitudinal axis Y-Y' of the prop and intersecting the longitudinal axis Y-Y' of the prop when the endoprosthesis is in its dilated state.

7. Device according to claim 3, wherein that the proximal guidance passage and the distal guidance passage are located substantially in an axial plane containing the axis of the endoprosthesis.

8. Device according to claim 7, wherein, when each retaining loop is in the release configuration thereof, the proximal guidance passage and the distal guidance passage are located in the region of the prop, substantially along the longitudinal axis Y-Y' of the prop.

9. Device according to claim 7, wherein the distal retention opening is located opposite the proximal retention opening with respect to the longitudinal axis Y-Y' of the prop, the distal guidance passage being placed in register with the distal retention opening and the proximal guidance passage being located in register with the proximal retention opening.

10. Device according to claim 7, wherein a proximal retaining loop extends radially away from the prop in a first direction, between the configuration in which the endoprosthesis is kept in the contracted state and the configuration in which the endoprosthesis is released, a distal retaining loop extending radially away from the prop, between the configuration in which the endoprosthesis is kept in the contracted state and the configuration in which the endoprosthesis is released, in a second direction away from the first direction.

11. Device according to claim 7, wherein the prop has a proximal end and a distal end in the region of which the retention openings are arranged, each wire-like tie comprising a control portion connected to a first end of the retaining loop and extending to the proximal end of the prop.

12. Method of preparation of a device according to claim 7, prior to its implantation in a duct through which blood flows, comprising the following steps:
    (a) keeping the endoprosthesis in a dilated state where the or each retaining loop is kept in its configuration in which the endoprosthesis is released, the longitudinal axis X-X' of the endoprosthesis being inclined with respect to the longitudinal axis Y-Y' of the prop when no external stresses are applied, the longitudinal axis X-X' of the endoprosthesis intersecting the longitudinal axis Y-Y' of the prop in the internal duct; then (b) tightening each retaining loop to bring it into the configuration thereof in which the endoprosthesis is kept in its contracted state against the prop, in order to implant the endoprosthesis in the duct through which the blood flows.

13. Method for implanting a device according to claim 7, in a duct through which blood flows, comprising the following steps:

introducing the endoprosthesis in its contracted state resting against the prop, the endoprosthesis being fixed substantially coaxially with the prop;

extending the retaining loops of the wire-like distal tie and of the wire-like proximal tie to pass the endoprosthesis in its dilated state, the axis X-X' of the endoprosthesis being inclined with the longitudinal axis Y-Y' of the prop and intersecting the longitudinal axis Y-Y' of the prop when the endoprosthesis is in its dilated state.

14. Device according to claim 2, wherein, when each retaining loop is in the release configuration thereof, the proximal guidance passage and the distal guidance passage are located in the region of the prop, substantially along the longitudinal axis Y-Y' of the prop.

15. Device according to claim 2, wherein the distal retention opening is located opposite the proximal retention opening with respect to the longitudinal axis Y-Y' of the prop, the distal guidance passage being placed in register with the distal retention opening and the proximal guidance passage being located in register with the proximal retention opening.

16. Device according to claim 1, wherein a proximal retaining loop extends radially away from the prop in a first direction, between the configuration in which the endoprosthesis is kept in the contracted state and the configuration in which the endoprosthesis is released, a distal retaining loop extending radially away from the prop, between the configuration in which the endoprosthesis is kept in the contracted state and the configuration in which the endoprosthesis is released, in a second direction away from the first direction.

17. Device according to claim 1, wherein the prop has a proximal end and a distal end in the region of which the retention openings are arranged, each wire-like tie comprising a control portion connected to a first end of the retaining loop and extending to the proximal end of the prop.

18. Device according to claim 17, wherein it comprises a retention rod which is disposed movably with respect to the prop between a retention position in which an active part of the rod is placed in register with each retention opening and a release position in which the active part of the rod is placed apart from each retention opening, each wire-like tie comprising a keeper loop attached to a second end of the retaining loop and engaged on the rod in its retention position.

19. Method of preparation of a device according to claim 1, prior to its implantation in a duct through which blood flows, comprising the following steps:

(a) keeping the endoprosthesis in a dilated state where the or each retaining loop is kept in its configuration in which the endoprosthesis is released, the longitudinal axis X-X' of the endoprosthesis being inclined with respect to the longitudinal axis Y-Y' of the prop when no external stresses are applied, the longitudinal axis X-X' of the endoprosthesis intersecting the longitudinal axis Y-Y' of the prop in the internal duct; then (b) tightening each retaining loop to bring it into the configuration thereof in which the endoprosthesis is kept in its contracted state against the prop, in order to implant the endoprosthesis in the duct through which the blood flows.

20. Method for implanting a device according to claim 1, in a duct through which blood flows, comprising the following steps:

introducing the endoprosthesis in its contracted state resting against the prop, the endoprosthesis being fixed substantially coaxially with the prop;

extending the retaining loops of the wire-like distal tie and of the wire-like proximal tie to pass the endoprosthesis in its dilated state, the longitudinal axis X-X' of the endoprosthesis being inclined with the longitudinal axis Y-Y' of the prop and intersecting the longitudinal axis Y-Y' of the prop when the endoprosthesis is in its dilated state.

* * * * *